United States Patent [19]
Santschi et al.

[11] Patent Number: 5,760,911
[45] Date of Patent: Jun. 2, 1998

[54] CONTINUOUS PARTICULATE EMISSIONS MONITOR CALIBRATOR

[75] Inventors: Mark Santschi, Lee's Summit; Brian Van Vickle, Pleasant Valley; Ted Reinsch, Kansas City, all of Mo.

[73] Assignee: BHA Group Holdings, Inc., Kansas City, Mo.

[21] Appl. No.: 464,827

[22] PCT Filed: Apr. 22, 1994

[86] PCT No.: PCT/US94/04492

§ 371 Date: Mar. 18, 1996

§ 102(e) Date: Mar. 18, 1996

[87] PCT Pub. No.: WO95/29399

PCT Pub. Date: Nov. 2, 1995

[51] Int. Cl.[6] .................................................. G01N 21/00
[52] U.S. Cl. ...................................... 356/442; 356/438
[58] Field of Search .................................. 356/437–439, 356/441–442, 335–336

[56] References Cited

U.S. PATENT DOCUMENTS

| | | | |
|---|---|---|---|
| 3,632,209 | 1/1972 | Kingman | 356/434 |
| 3,779,650 | 12/1973 | Crowley | 356/433 |
| 3,825,345 | 7/1974 | Lorenz . | |
| 3,879,129 | 4/1975 | Inoue . | |
| 4,135,821 | 1/1979 | Pechin et al. . | |
| 4,420,256 | 12/1983 | Fladda et al. . | |
| 4,583,859 | 4/1986 | Hall, II . | |
| 5,028,790 | 7/1991 | McGowan et al. | 356/438 |

*Primary Examiner*—David C. Nelms
*Assistant Examiner*—Amanda Merlino
*Attorney, Agent, or Firm*—Kokjer, Kircher, Bowman & Johnson

[57] ABSTRACT

A device (10) and method for monitoring particulate (22) flowing through a conduit (20) has a transmitter (16) and a receiver (18) positioned in optical alignment on opposite sides of the conduit (20). A light beam (50) is transmitted across conduit (20) from the transmitter (16) to the receiver (18). Particulate (22) flowing through conduit (20) interrupts light beam (50) causing a signal to be generated from which particulate concentration is determined. A calibrator assembly (40) has a motor (64) adapted to move a filter (100) having a selected percentage opacity within the path of light beam (50). Movement of the filter (100) modulates light beam (50) and a signal corresponding to the concentration associated with the percentage opacity is generated.

13 Claims, 3 Drawing Sheets

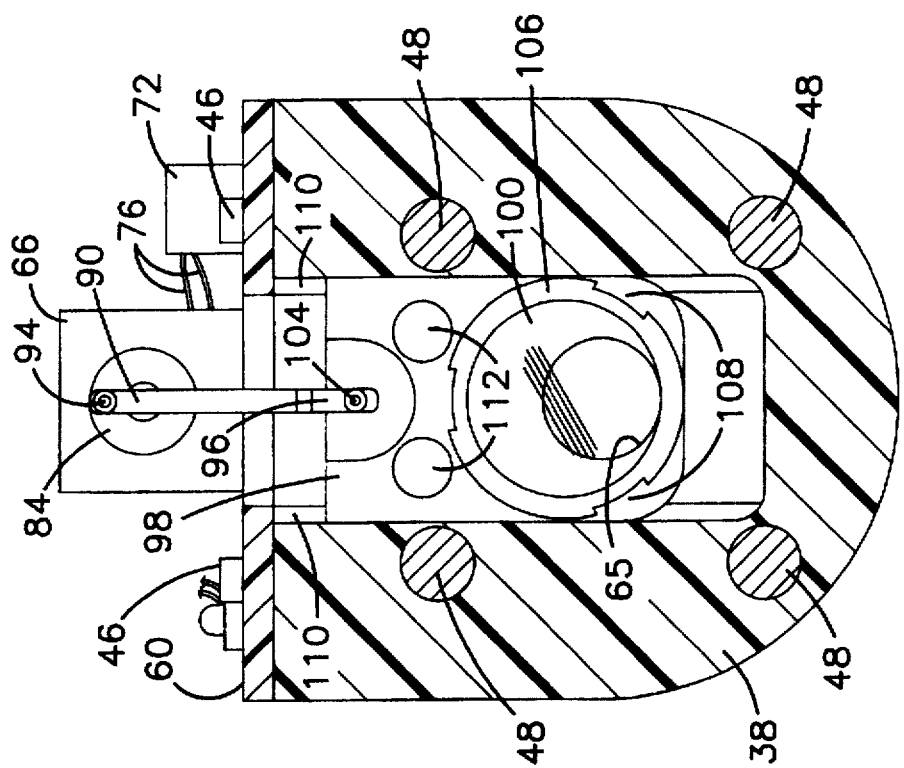
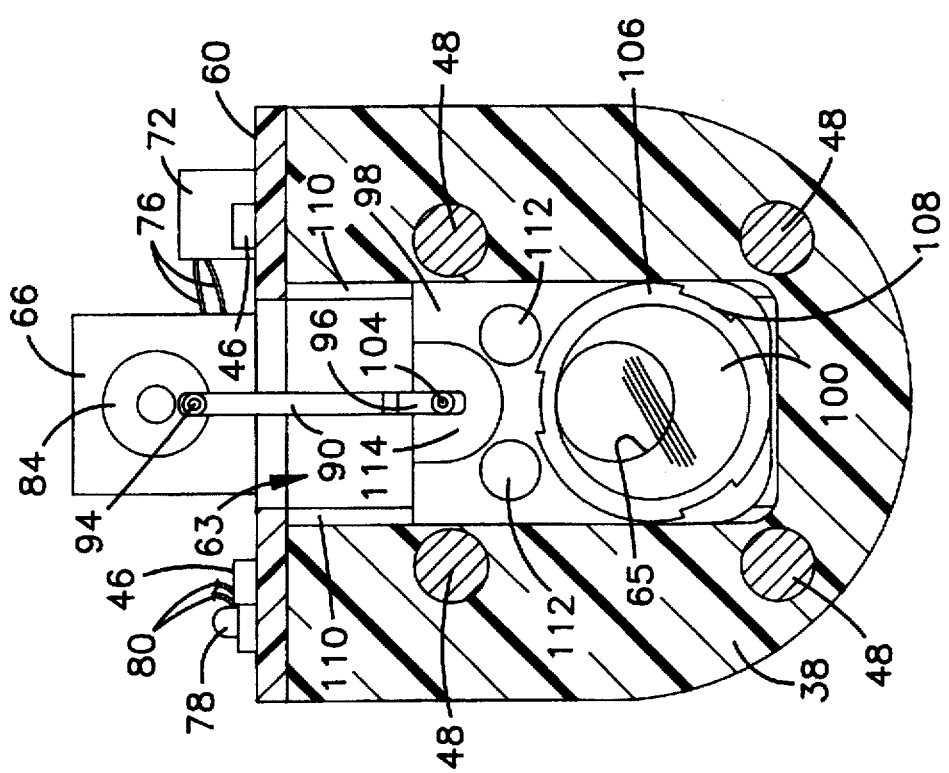

CONTINUOUS PARTICULATE EMISSIONS MONITOR CALIBRATOR

BACKGROUND OF THE INVENTION

1. Field of the Invention

The present invention relates in general to a device for monitoring particulates passing through a duct, such as for instance, passing through a duct in a baghouse discharge or from an industrial stack. In particular, the present invention relates to a device for monitoring the frequency at which a light shown across an emissions duct is interrupted. More specifically, the present invention is directed to a method, system, and device for correlating a selected percentage opacity with its associated reading in concentration units in connection with such an emissions monitor.

2. Description of the Related Art

Emissions monitoring has become increasingly important in response to strict environmental regulations and increased public awareness of environmentally-safe industrial processes. Numerous types of devices have been developed for monitoring particulate emissions in industrial applications. In general, these devices monitor the particulate flowing through a duct or stack, and particularly, monitor the amount of particulate being emitted. In this regard, the greater the concentration or percentage of particulate relative to the emissions as a whole, the greater the quantity of pollutants entering the atmosphere. If an industrial process emits pollutants into the air in excess of a maximum permissible amount as set by the Environmental Regulators, great expense associated with fines and perhaps shut-down can be incurred. Accordingly, monitoring particulate emissions is extremely important for maintaining a clean environment and transacting business in accordance with the law.

Numerous devices and systems have been developed for monitoring particulate emissions. One conventional system utilizes what is called opacity technology. In general, opacity devices shine light from a transmitter located on one side of a stack or duct to be monitored to a receiver located on the opposite side of the duct in optical alignment with the transmitter. As dust travels through the stack or duct, the dust both scatters and absorbs some of the light provided by the opacity device. By comparing the brightness or intensity of the light shining across the stack or duct when no emissions are occurring with the dimmer brightness or intensity of light associated with dust traveling through the stack, a percentage opacity measurement can be obtained. Percentage opacity is a commonly used unit for measuring emissions. Another type of emissions monitoring device, called an impaction or triboelectric device, utilizes an earth-grounded probe inserted into a stream of particles to be monitored. As each particle impinges onto the probe, a transfer of electrical charge occurs which results in an electrical current at the probe. Monitoring the current results in a relative emissions measurement.

The foregoing devices have numerous drawbacks which reduce their effectiveness and desirability. For instance, opacity systems, which are based upon the amount of light energy detected through passing dust, quickly become inaccurate as lenses used by the device become caked with dust. In other words, as particulates build up on the sensors, the opacity device is unable to distinguish between moving dust being emitted from the stack or duct and stationary dust which continues to settle on the sensors. Accordingly, the reading in such an environment is inaccurate. In this regard, an opacity device having dust accumulated on the sensors will show an emissions reading even when no emissions are occurring. Accordingly, the sensors of an opacity device require constant cleaning. Similarly, impaction or triboelectric devices, which have a probe positioned within the dust stream, quickly become dirty and must be repeatedly cleaned. Periodic cleaning of the foregoing devices, in addition to requiring repeated extensive time and effort, increase the cost of using such devices.

A more recent device for monitoring particulate flowing through a duct or stack uses a DC light beam shining across the duct or stack to be monitored. However, unlike the opacity devices which monitor light energy, these continuous particulate monitoring devices monitor interruptions in the light beam caused by particulates passing through the light beam. In other words, as a particulate passes through the light beam shining across the stack or duct, the light beam is temporarily broken. Accordingly, as particulate flows through the duct or stack, it passes through the light beam causing the light beam to flicker or modulate. A receiver for receiving the light beam monitors this flicker or modulation and a signal is generated for use in computing the frequency of interruptions of the light beam. The concentration of particulate is proportional to the frequency of modulation. Since continuous particulate monitors of this type are not concerned with the intensity of the light, but rather the interruption of the light beam, particulate accumulated on the light transmitter or receiver of the monitor does not reduce the effectiveness or accuracy of the monitor. Furthermore, it is known to increase the intensity of the light beam proportional to the amount of stationary particulate accumulated at the transmitter and receiver to insure consistent and accurate particulate monitoring. Accordingly, a continuous particulate monitor of this type for monitoring an interrupted light beam requires cleaning far less frequently than other conventional emissions monitoring devices. Moreover, as stated, unlike an opacity system, such a monitor remains accurate despite particulates settling on the light sensors. In fact, it has been found that such a monitor remains effective even when over 90% of the transmitted light is blocked with particulates, such as dust.

Despite the advantages of continuous particulate monitors utilizing an interrupted light beam for monitoring, these devices, when calibrated with an isokinetic test, provide an emissions measurement in units of concentration, not in units of percentage opacity. Conventional practice, particularly in the United States, is to rate emissions in percentage opacity. Accordingly, the need exists for a continuous particulate monitor, which utilizes light beam interruption, which can be calibrated for percentage opacity readings. Particularly, the need exists for a calibration device, for use with emissions monitors using light beam interruption techniques, for calibrating the device for percentage opacity readings. With such a device, the concentration of particulate flowing through a duct or stack relative to a selected percentage opacity reading could be determined. The present invention provides such a device and fills the foregoing and other needs.

SUMMARY OF THE INVENTION

It is an object of the present invention to provide a continuous particulate monitor which is inexpensive and easy to manufacture, and which is easy to use and install.

It is a further object of the present invention to provide a continuous particulate monitor, which utilizes light beam interruption, which can be calibrated for percentage opacity readings.

It is a further object of the present invention to provide a calibration or correlating device and method, for use with an emissions monitor using light beam interruption techniques, for calibrating the monitor for percentage opacity readings, and specifically, for correlating a selected percentage opacity with a concentration reading.

It is a further object of the present invention to provide a device and method for determining the concentration of particulate flowing through a duct or stack relative to a selected percentage opacity.

These and other objects are achieved by a continuous particulate monitor, of a light beam interference type, having a calibrator assembly for correlating a known percentage opacity with its associated reading in concentration units. Particularly, the monitor has a transmitter and a receiver positioned in optical alignment on opposite sides of a duct or stack to be monitored. The transmitter transmits a beam of light across the duct or stack where it is received by the receiver. As particulates pass through the light beam, the light beam is interrupted. The transmitter and receiver are connected to processing hardware. A signal indicative of the frequency at which the light beam is interrupted by particulates is generated and sent to the processing hardware. The processing hardware includes a display for visually displaying data indicative of the frequency at which the light beam is interrupted. In other words, the modulation of the light signal in the stack or duct caused by passing particulates provides a basis for determining the concentration of particulates flowing through the stack or duct. Preferably, the hardware comprises a central processing unit for calculating the concentration of particulates based upon knowledge of the type of particulates flowing through the system and the dimensions of the stack or duct.

A calibrator assembly is positioned between either the transmitter or the receiver and the stack or duct to be monitored. The calibrator assembly of the present invention is a device for calibrating the particulate monitor for readings in percentage opacity. In this regard, the particulate monitor displays data indicative of the concentration of particulates flowing through the stack or duct being monitored. Since it is desirable to know the percentage opacity reading associated with particulate flowing through the stack or duct, and particularly, since it is desirable to know when the emissions reach the permitted percentage opacity limit, the present invention provides means for calibrating the particulate monitor so that the particulate concentration reading associated with a selected percentage opacity (e.g., the upper permitted opacity limit) can be determined.

The calibrator assembly has a calibrator body with a channel-aperture therethrough. The aperture is placed in alignment with the light beam transmitted from the transmitter and to the receiver so that light is transmitted through the aperture of the calibrator body. A channel extends from the upper, outer exterior of the calibrator body to the central aperture of the calibrator body. The channel is adapted to receive a filter. The filter is connected to a filter holder assembly, which is in turn connected to a motor. When assembled, the filter is positioned within the channel in alignment with the calibrator aperture such that any light passing through the aperture must also pass through the filter. When the motor is activated, the filter moves substantially upwardly and downwardly in a portion of the space defined by the channel in the calibrator, although the filter itself remains in complete coverage of the central aperture of the calibrator.

In use, a filter having a known opacity is placed into the channel in alignment with the central aperture of the calibrator body. To calibrate the monitor for a percentage opacity reading, the monitor is reset to zero, and the calibrator motor is turned on. As a result, the filter is placed in motion. Once the filter is in motion, the receiver perceives the filter as particulates flowing through the dust or stack. A reading in accordance with the amount of particulate detected is thereby obtained. Since the percentage opacity of the filter is known, the concentration reading obtained is equivalent to that known, selected percentage opacity. As a result, the operator now has knowledge of the concentration reading corresponding to the percentage opacity of the filter selected.

BRIEF DESCRIPTION OF THE DRAWINGS

The objects and features of the invention noted above are explained in more detail with reference to the drawings, in which like reference numerals denote like elements, and in which:

FIG. 4 is a cross-sectional view taken along lines 4—4 of FIG. 3; and

FIG. 5 is a cross-sectional view of the calibrator assembly of the present invention for illustrating movement of the filter.

DETAILED DESCRIPTION OF THE INVENTION

Figure 1:
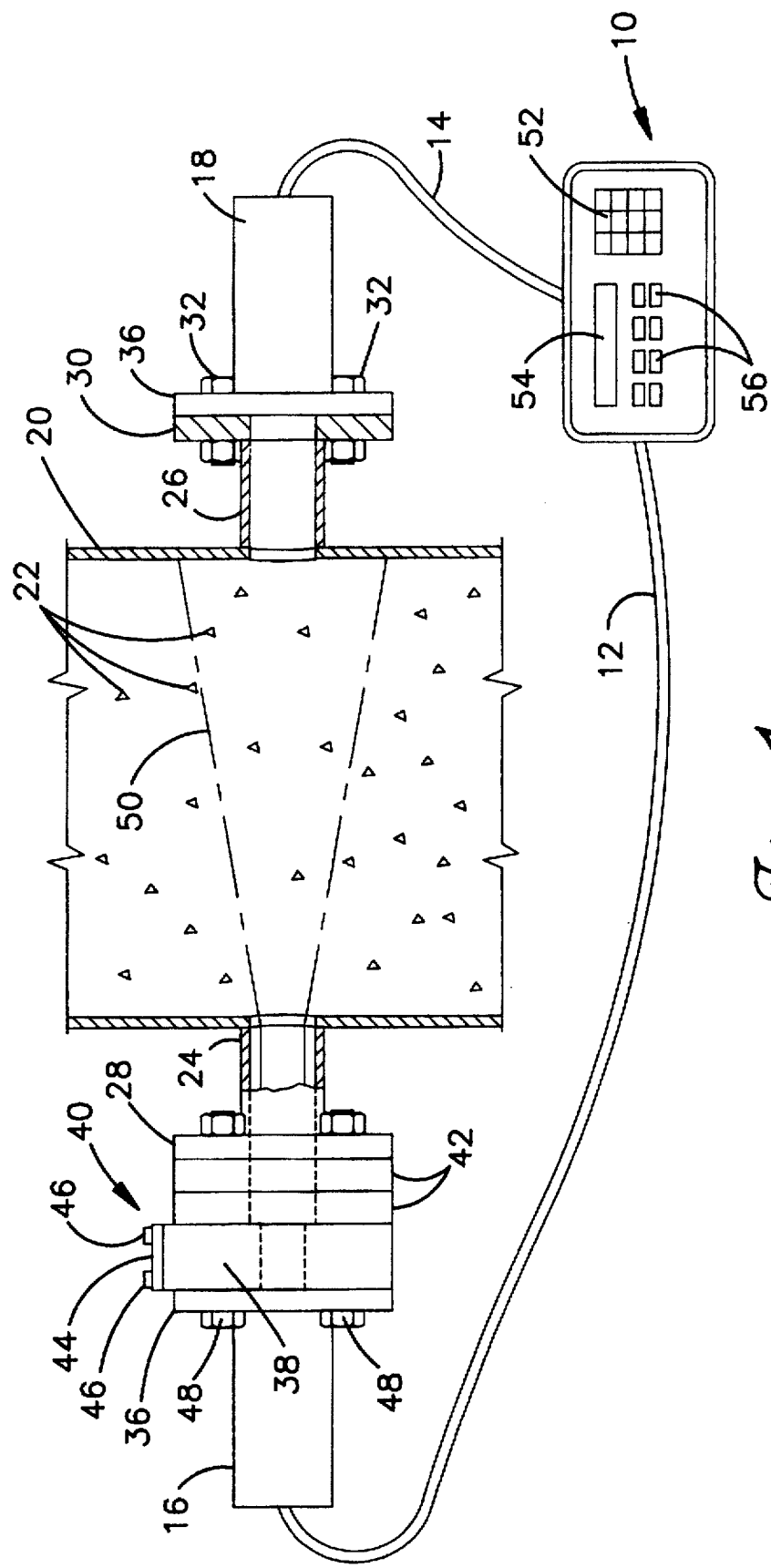
FIG. 1 is a schematic view of a continuous particulate monitor with calibration assembly, with the present invention positioned on a stack or duct for monitoring particulate flowing therethrough.

With reference initially to FIG. 1, a continuous particulate monitor of the present invention is denoted generally by reference numeral 10. Monitor 10 has connected thereto by wires 12, 14, a transmitter 16 and a receiver 18, respectively. As shown, transmitter 16 and receiver 18 are placed in optical alignment with each other on opposite sides of a stack or duct 20. It will be appreciated that stack or duct 20 comprises a conduit for transmitting particulates resulting from industrial processes. For instance, stack 20 may be an industrial smoke stack for passing emissions into the atmosphere. Alternatively, duct 20 may comprise a duct in an industrial process, such as a baghouse discharge duct. Furthermore, it should be appreciated that the conduit may take on shapes other than the cylindrical shape shown. Particulates 22 are shown flowing through the duct 20.

As shown in FIG. 1, duct 20 has a pair of pipes 24, 26 extending outwardly therefrom. Each pipe has a respective flange 28, 30 positioned at its outermost end. Prior particulate monitors of a type for sensing light beam interference, such as those marketed under product line CPM by BHA Group, Inc., Kansas City, Mo., provide for coupling a transmitter 16 and receiver 18 directly to respective flanges 28, 30. For instance, as shown in FIG. 1, continuous particulate monitor 10 of the present invention, which preferably utilizes such a CPM device by BHA Group, Inc., is shown with a flange 34 of receiver 18 coupled by bolts 32 to flange 30 of pipe 26.

In accordance with the principles of the present invention, transmitter 16 has a flange 36 adjacent a calibrator body 38 of a calibrator assembly 40 of the present invention. Preferably positioned between calibrator body 38 and flange 28 are one or more high-temperature insulators, such as the pair of temperature insulators 42.

As shown in FIG. 1, calibrator assembly 40 is comprised of a calibrator body 38 and a weather cap 44 which is bolted by bolts 46 to calibrator body 38. Transmitter 16, calibrator body 38, and insulators 42 are connected with flange 28 by bolts 48. It will be appreciated by those skilled in the art that insulators 42 are optional, and that additional insulators could be provided between the flange 30 of pipe 26 and the flange 36 of receiver 18. Additionally, it should be understood that calibrator assembly 40 may be positioned at the transmitter 16 as shown in FIG. 1, or alternatively, may be positioned at the receiver 18. Principles of operation of calibrator assembly 40 are not dependent upon its location.

It is seen that light transmitted from transmitter 16 shines through apertures positioned through calibrator body 38, insulators 42, and flange 28 of pipe 24. A light beam 50 shines across the stack or duct 20 where it is received by receiver 18. Monitor 10 is provided with a keypad 52, display 54, and further operating controls 56.

In accordance with the general operation of continuous particulate monitor 10, light beam 50 is transmitted across duct 20 from transmitter 16 to receiver 18. As particulates 50, traveling through duct 20, interrupt light beam 50, receiver 18 detects the interruption of the light beam, and generates a signal indicative of the frequency of interruption of light beam 50. The signal is sent to monitor 10. It will be appreciated by those skilled in the art that monitor 10, such as those manufactured under the CPM product line by BHA Group, Inc., provide means for then displaying on display 54 data indicative of the frequency of light beam interruption. From this data, the concentration of particulates flowing through the duct 20 can be determined. Alternatively, monitor 10 preferably comprises a central processing unit for calculating particulate concentration utilizing the data received from receiver 18. In this regard, upon installation and start-up of monitor 10, an actual sample of the particulates flowing through duct 20 is taken and analyzed for making various determinations, such as the concentration of particulates flowing through the duct 20, and the type of particulates flowing through duct 20. The actual particulate concentration thereby obtained is compared with the data provided by the monitor 10, and monitor 10 is adjusted if necessary to the actual value of the concentration obtained from the sample. As a result, monitor 10 is thereby accurately calibrated for measuring the concentration of particulate flowing through duct 20.

It should be appreciated that the foregoing description, with the exception of the calibrator assembly 40, specifies the generally preferred components for a particulate monitor of the type for detecting light beam interference. With reference now to FIGS. 2–5, additional components and operation of calibrator assembly 40 is discussed.

Figure 2:
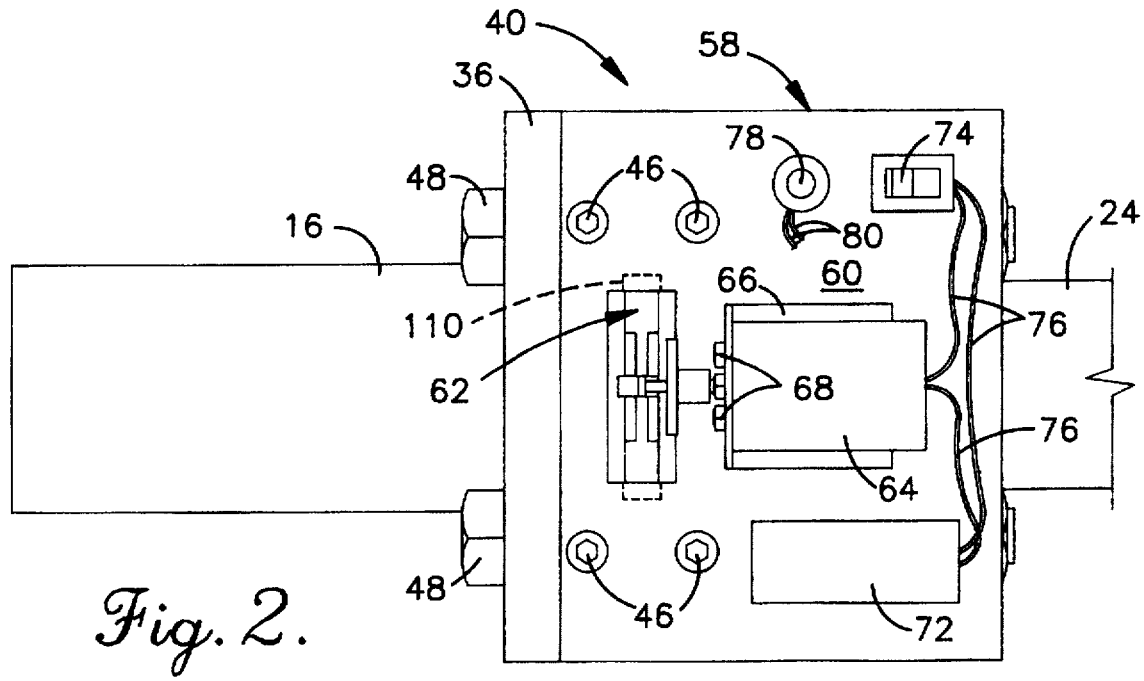
FIG. 2 is a top plan view of a portion of the particulate monitor of the present invention, and particularly, of a motor platform of the calibrator assembly of the present invention.
Figure 3:
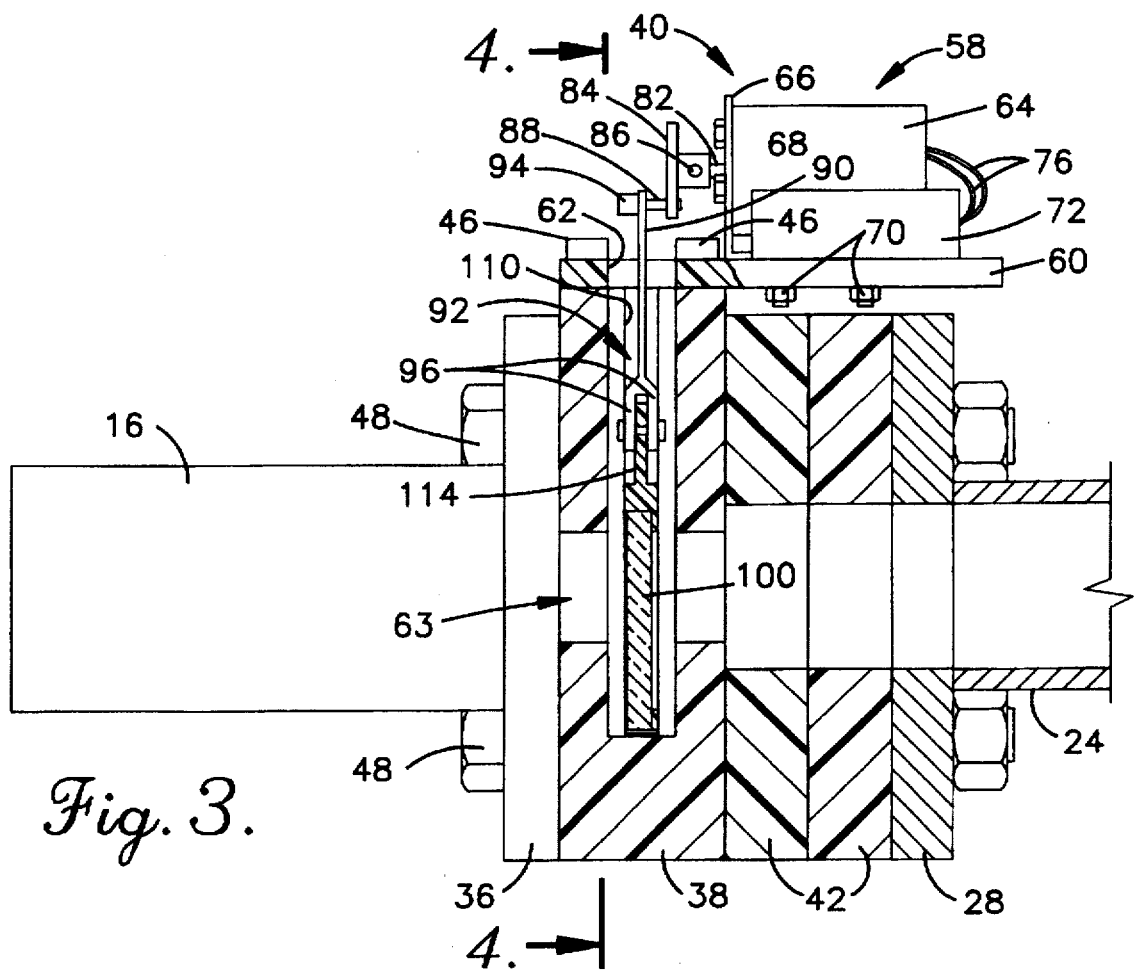
FIG. 3 is a cross-sectional view taken along lines 3—3 of FIG. 2.

FIG. 2 shows an enlarged top-plan view of the calibrator assembly 40 of the present invention, with weather plate 44 (FIG. 1) removed, and motor platform and assembly 58 mounted by bolts 46 in its place. With reference also to FIG. 3, motor platform and assembly 58 comprises a platform 60 having a slot 62 formed therein. Slot 62 provides access to channel 63 formed in calibrator body 38. A motor 64 is mounted to a bracket 66 by bolts 68. Bracket 66 is connected to platform 60 by bolts 70. A battery pack 72 and an on-off switch 74 are connected by wires 76 to motor 64. A low-voltage indicator light 78 is connected by wires 80 to battery pack 72 for indicating when the voltage supplied by battery pack 72 falls below a preselected level.

Motor 64 preferably provides a rotating output at a preselected RPM rating. Rod member 82 extends outwardly from motor 64, through an aperture (not shown) in brackets 66. Upon activation of motor 64, rod member 82 rotates. Eccentric 84 is connected to rod member 82 by a pin connection 86. Eccentric 84 has an outwardly extending pin member 88 which is threaded through an aperture (not shown) in an upper portion of arm 90 of filter holder assembly 92. A cap 94 is positioned on the outermost end of pin member 88 for maintaining filter holder assembly 92 in place.

Arm 90 of filter holder assembly 92 has a pair of prongs 96 at its lowermost end. Prongs 96 grip filter holder 98 having a filter 100 positioned therein. A pin is threaded through prongs 96 and a small pin receiving aperture in an upper central portion of filter holder 98. It will be appreciated that filter 100 is made from glass or plastic. Filter 100 has an outer rim 106. Filter holder 98 has a plurality of locking tabs 108 for engaging the outer rim 106 of filter 100 for holding filter 100 in place. In this regard, it will be appreciated that filter 100 merely snap fits into filter holder 98.

As shown in FIGS. 2–5, grooves are provided at the ends of channel 63 of calibrator body 38 to provide guide rails 110 at the outer edges of channel 63. In this way, filter holder 98 fits substantially snug within the grooves of channel 63 of calibrator body 38, and is guided by guide rails 110 during operation of the device.

As shown in FIGS. 4 and 5, filter holder 98 is preferably provided with a pair of balancing apertures 112. Balancing apertures 112 reduce the weight of filter holder 98 in a balanced fashion. Further, filter holder 98 is preferably more narrow at its uppermost end to provide a gripping area 114 for prongs 96 of arm 93.

In operation, monitor 10 monitors particulates flowing through stack or duct 20. This operation is described in detail above, and it should be understood that a light beam transmitted across stack or ducts 20 from transmitter 16 to receiver 18 is interrupted by passing particulate. Receiver 18 generates a signal indicative of the frequency of modulation of the light beam caused by the passing particulates, and monitor 10 provides data indicative of the concentration of particulate passing through duct or stack 20. In this regard, the concentration reading is in any preferred units, such as for instance, grams per cubic meter. Operation of the present invention for calibrating monitor 10 for a percentage opacity reading is now described.

To calibrate monitor 10 for a selected percentage opacity reading, weather cap 44 is removed from calibrator body 38 by removing bolts 46. In its place, motor platform and assembly 58, complete with filter holder assembly 92, is bolted into place by bolts 46. Motor platform and assembly 58 is positioned such that slot 62 in motor platform 60 aligns with channel 63 extending into calibrator body 38. Filter holder assembly 92 is positioned such that arm 90 extends from its connecting point on pin 88 of eccentric 84 through slot 62 of platform 60 and into channel 63 of calibrator body 38. The components of the present invention are dimensioned such that filter 100 is positioned in alignment, and extends about the periphery of, aperture 65 in calibrator body 38.

Motor 64 is activated by turning on-off switch 74 to the on position. When activated, motor 64 provides a rotating output, at a rated revolutions per minute, at rod member 82. As a result, eccentric 84 rotates. As a result, arm 90, which is connected to pin member 88 positioned near a peripheral edge of eccentric 84, travels about the periphery along with its pin connection point 88. This causes the arm 90 to reciprocatingly stroke generally upwardly and downwardly, thereby causing the entire filter holder assembly 92, and particularly the filter holder 98 to move upwardly and downwardly within channel 63 of calibrator body 38. Movement of filter holder 98 is illustrated in this manner in FIGS. 4 and 5.

As shown in FIG. 4, arm 90 is at the lower-most portion of its stroke as pin member 88 on eccentric 84 is at its lower-most position. In such a position, filter 100; although remaining in a position such that it entirely blocks the channel-aperture 65 of calibrator body 38, is displaced downwardly in relation to the channel aperture 65. By contrast, as shown in FIG. 5, as arm 90 reaches the upper-most position of its stroke, filter holder 98 has been drawn upwardly such that filter 100 is displaced upwardly in relation to channel-aperture 65 of calibrator body 38. However, as shown in FIG. 5, filter 100 is still positioned such that it blocks the entire channel aperture 65 of calibrator body 38.

To properly calibrate monitor 10, filter 100 is preselected based upon its known percentage opacity rating. Although it should be appreciated that any percentage opacity filter could be selected, it is preferred to select a filter having a percentage opacity rating equivalent to the upper percentage opacity limit of permissible emissions from the system in which the present invention is utilized. Accordingly, for instance, if a particular emissions system is permitted to emit up to 20% opacity, a 20% opacity filter may be selected. A reading at monitor 10 taken through the moving filter 100, although in concentration units, will be equivalent to the opacity rating of the selected filter. As a result, in this example, the concentration reading corresponding to 20% opacity is obtained, and the future use of the device can monitor for that threshold limit. It will be appreciated that data associated with the threshold limit can be used for triggering alarms, or shut down circuitry, which may be used with monitor 10.

It will be appreciated that numerous possible embodiments and variations may be accomplished without departing from the spirit and scope of the present invention. In this regard, it is necessary only that the filter 100 is positioned within the light beam 50 between the transmitter 16 and the receiver 18. Accordingly, its precise positioning within that light beam 50 is not critical. Additionally, although it is necessary for the filter to remain in motion at a rate >1.5 m/sec for proper calibration, it will be appreciated that numerous possible devices, including various types of motor assemblies, can be provided for moving filter 100 and maintaining filter 100 in motion.

As discussed above, it is necessary for filter 100 to remain in motion for proper calibration since, if filter 100 were maintained static, receiver 18 would perceive the filter as accumulated dust on the transmitter or receiver. Accordingly, monitor 10 would respond by merely increasing the power to transmitter 16 or increasing the brightness of light beam 50. Since monitor 10 senses only moving particulates, it is necessary for filter 100 to be in motion for monitor 10 to sense that which is blocking the light beam. In this regard, it should be understood that filter 100, which is obviously tinted to a selected percentage opacity, is viewed by the receiver as a multitude of very fine particulates moving through duct or stack 20.

In accordance with the principles of the present invention, it has been found that it is necessary for filter 100, during the calibration procedure, to move in excess of 1.5 meters per second. It is important to maintain the filter movement at greater than 1.5 meters per second to ensure that the receiver senses moving particulate. If the filter is moved any slower than 1.5 meters per second, the receiver will no longer sense motion, but rather, monitor 10 will perceive the filter as particulate accumulation on the transmitter 16 or receiver 18. Accordingly, to ensure that a proper speed filter movement is maintained, motor 66 and the length of the necessary stroke of arm 90, keeping in mind the dimensions of filter 100 and channel aperture 65, are selected so as to ensure that movement of the filter is in excess of 1.5 meters per second. Additionally, by utilizing the ratings of the motor, traditional voltage monitoring circuitry (not shown) is coupled with the battery pack 72. When the battery drops below a voltage threshold equated with the minimum RPM's necessary for maintaining movement of filter 100 at greater than 1.5 meters per second, indicator light 78 emits light to visually indicate that the battery pack 72 needs to be replaced. It will be readily understood that other types of power supplies, other than battery pack 72, may be utilized.

In the preferred embodiment, a 12-volt DC motor with a rotating output up to 1,000 RPM's, such as manufactured by Philips, of Belgium is supplied with three DC volts. The visible portion of filter 100 (i.e., within outer rim 106) in such an embodiment preferably has a 1.625" diameter, channel aperture 63 has a diameter of 1", and the central-most portion of channel aperture 63 is positioned 3.813 inches from an axis extending from rotating output member 82 of motor 64. Eccentric 84 preferably has a diameter of 0.88", and pin member 88 is preferably displaced 0.313" from the central axis thereof. Accordingly, one full stroke of arm 90 is 0.626", or approximately ⅝ inches.

Additionally, although not shown in the drawing for illustrative reasons, it will be appreciated that selected components of the present invention, such as for instance, the motor, the battery pack, and the filter holder assembly may be retained in a housing.

Additionally, it should be understood that the emissions need not be ceased to calibrate the monitor. In this regard, as emissions are passing through the duct or stack to be monitored, monitor 10 is preferably reset to a zero reading. At this point, calibrator assembly 40 is activated and the concentration reading at the display of monitor 10 is taken. It is known that this reading corresponds to the percentage opacity of the filter utilized in the calibrator assembly 40. Alternatively, the step of resetting monitor 10 to zero can be omitted, calibrator assembly 40 can be activated, and the concentration reading associated with the selected percentage opacity filter can be calculated from the difference in readings with, and without, the calibrator assembly 40 in operation.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

We claim:

1. A device for monitoring particulates flowing through a conduit, said device comprising: means for shining a beam of light across the conduit; means for detecting modulation of said light beam caused by particulates passing through said light beam, including means for generating a signal indicative of the concentration of particulate flowing through said conduit; means for correlating a selected percentage opacity with its associated reading in concentration units; and a filter having a selected percentage opacity positioned in optical alignment with said light beam; and means for reciprocatingly moving said filter to provide modulation to said light beam.

2. The device as set forth in claim 1, said correlating means further comprises: a filter assembly for engaging said filter, wherein said means for moving said filter moves said filter assembly with said filter engaged therein; and a body member for guiding said filter assembly during movement of said filter assembly.

3. The device as set forth in claim 2 wherein said body member has a first face and a second face and an aperture extending through said body from said first face to said second face, said body further having a channel extending from an outer surface of said body to intercommunicate with said aperture, whereby said filter assembly is positioned within said channel such that said filter is aligned with said aperture extending through said body.

4. The device as set forth in claim 1, said moving means further comprising means to move said filter at a speed in excess of 1.5 meters per second.

5. The device as set forth in claim 4 further comprising means for indicating when the speed of said filter falls below a preselected level.

6. In an apparatus for monitoring particulate flowing through a conduit, said apparatus providing a light beam across said conduit and comprising a sensor for sensing modulation of the light beam caused by particulate passing through the light beam, a device for correlating a selected percentage opacity with its associated reading in concentration units, said device comprising: a filter having a selected percentage opacity positioned such that said light beam passes through said filter; and means for reciprocatingly moving said filter such that said sensor senses modulation of said light beam caused by said reciprocatingly moving filter.

7. The device as set forth in claim 6 further comprising: a filter assembly for engaging said filter, wherein said means for moving said filter moves said filter assembly with said filter engaged therein; and a body member for guiding said filter assembly during movement of said filter assembly.

8. The device as set forth in claim 7 wherein said body member has a first face and a second face and an aperture extending through said body from said first face to said second face, said body further having a channel extending from an outer surface of said body to intercommunicate with said aperture, whereby said filter assembly is positioned within said channel such that said filter is aligned with said aperture extending through said body.

9. The device as set forth in claim 7, said moving means further comprising means to move said filter at a speed in excess of 1.5 meters per second.

10. The device as set forth in claim 9 further comprising means for indicating when the speed of said filter falls below a preselected level.

11. A method for correlating a selected percentage opacity with its associated concentration reading in a device which monitors particulate flowing through a conduit by detecting modulation of a light beam caused by particulate interrupting the light beam, said method comprising the steps of: placing a filter with a selected percentage opacity in alignment with said light beam so that said light beam passes through said filter; reciprocatingly moving said filter so that said filter modulates said light beam; and sensing the modulation of the light beam caused by said filter and determining therefrom the associated concentration reading.

12. The method as set forth in claim 11 further comprising the step of comparing said associated concentration reading with said selected percentage opacity.

13. The method as set forth in claim 12 further comprising the step of resetting said device to a zero setting prior to performing the step of moving said filter.

* * * * *